(12) United States Patent
Lemburg et al.

(10) Patent No.: US 10,393,630 B2
(45) Date of Patent: Aug. 27, 2019

(54) AUTOMATED MULTIPLE SAMPLE PROCESSOR HAVING A PLURALITY OF PISTON PUMPS

(71) Applicant: Alfred-Wegener-Institut Helmholtz-Zentrum fuer Polar-und Meeresforschung, Bremerhaven (DE)

(72) Inventors: Johannes Lemburg, Bremerhaven (DE); Erich Dunker, Schiffdorf (DE)

(73) Assignee: ALFRED-WEGENER-INSTITUT HELMHOLTZ-ZENTRUM FUER POLAR-UND MEERESFORSCHUNG, Bremerhaven (DE)

( * ) Notice: Subject to any disclaimer, the term of this patent is extended or adjusted under 35 U.S.C. 154(b) by 0 days.

(21) Appl. No.: 16/095,966

(22) PCT Filed: Apr. 11, 2017

(86) PCT No.: PCT/DE2017/100290
§ 371 (c)(1),
(2) Date: Oct. 24, 2018

(87) PCT Pub. No.: WO2017/186214
PCT Pub. Date: Nov. 2, 2017

(65) Prior Publication Data
US 2019/0137365 A1    May 9, 2019

(30) Foreign Application Priority Data

Apr. 26, 2016   (DE) .................. 10 2016 005 055

(51) Int. Cl.
*G01N 1/14*   (2006.01)
*G01N 1/24*   (2006.01)
(Continued)

(52) U.S. Cl.
CPC ................ *G01N 1/14* (2013.01); *F04B 1/00* (2013.01); *F04B 9/02* (2013.01); *G01N 1/24* (2013.01); *G01N 2001/1427* (2013.01)

(58) Field of Classification Search
CPC ...... G01N 2001/1427; G01N 1/14; F04B 1/16
See application file for complete search history.

(56) References Cited

U.S. PATENT DOCUMENTS 3,884,081 A   5/1975   Griffith
4,116,067 A   9/1978   Pankratz
(Continued)

FOREIGN PATENT DOCUMENTS

FR         3004257 A1   10/2014
WO    WO 9630740 A1   10/1996
(Continued)

*Primary Examiner* — Lisa M Caputo
*Assistant Examiner* — Alex T Devito
(74) *Attorney, Agent, or Firm* — Leydig, Voit & Mayer, Ltd.

(57) ABSTRACT

An automated multiple-sample processor for fluid samples includes a plurality of piston pumps which have a sample opening, a cylindrical housing and an axially displaceable piston and which are removably mounted in a support frame. The two spiral springs are both designed either as extension springs or as compression springs. In the case the two spiral springs are provided as the extension springs with a release lever in a first installation position, the triggering of the release lever results in the piston being pushed into the cylindrical housing. In the case the two spiral springs are provided as the compression springs with the release lever in a second installation position, which is rotated by 180° with respect to the first installation position, the triggering of the release lever results in the piston being pushed out of the cylindrical housing.

11 Claims, 4 Drawing Sheets

(51) Int. Cl.
*F04B 1/00* (2006.01)
*F04B 9/02* (2006.01)

(56) References Cited

U.S. PATENT DOCUMENTS

| | | |
|---|---|---|
| 4,288,206 A | 9/1981 | Tigwell et al. |
| 5,201,720 A | 4/1993 | Borgia et al. |
| 5,800,405 A | 9/1998 | McPhee |
| 6,187,530 B1 | 2/2001 | Scholin |
| 6,840,121 B2 | 1/2005 | Thomas et al. |
| 2006/0069354 A1 | 3/2006 | Buenger et al. |
| 2010/0247378 A1 | 9/2010 | Cerra et al. |

FOREIGN PATENT DOCUMENTS

| | | |
|---|---|---|
| WO | WO 2012085580 A1 | 6/2012 |
| WO | WO 2015011579 A2 | 1/2015 |

AUTOMATED MULTIPLE SAMPLE PROCESSOR HAVING A PLURALITY OF PISTON PUMPS

CROSS-REFERENCE TO PRIOR APPLICATIONS

This application is a U.S. National Stage Application under 35 U.S.C. § 371 of International Application No. PCT/DE2017/100290 filed on Apr. 11, 2017, and claims benefit to German Patent Application No. DE 10 2016 005 055.1 filed on Apr. 26, 2016. The International Application was published in German on Nov. 2, 2017, as WO 2017/186214 A1 under PCT Article 21(2).

FIELD

The invention relates to an automated multiple-sample processor for fluid samples, comprising a plurality of piston pumps which have a sample opening, a cylindrical housing and an axially displaceable piston and which are removably mounted in a support frame, each piston being connected to at least one spiral spring by means of the free end of said piston that is remote from the sample opening, which spring is supported in the support frame and can be fixed in a tensioned initial position by means of a lock which, for each piston pump, has a release lever that can be triggered by a driver on a rotatable shaft, the triggering of the release lever resulting in the piston being displaced in the cylindrical housing.

BACKGROUND

Automated multiple-sample processors designed as multiple-sample collectors are used to automatically take samples of fluids, i.e. liquids or gases. The automatic nature of this process makes it possible for samples to be taken even in inaccessible locations; for example, water samples can be taken in the deep sea, known as "water sample collectors" (WSC). Experiments of this kind at the sample location generally involve an enclosed water volume being defined by a benthic chamber and a sample then being drawn in the chamber. A multiple-sample collector allows a plurality of samples to be taken simultaneously, but also sequentially at predefined temporal intervals (fixed, yet time-resolved sampling). Key aspects of the technical implementation of multiple-sample collectors of this kind are the sampler itself and the automatic drive during sampling. The invention relates in particular to piston pumps as samplers, the pistons of which can be displaced by a spring drive. A spring drive allows automatic triggering without a direct power supply. Said supply is then only required to trigger the springs, but has suitably smaller dimensions than a direct drive, and therefore the multiple-sample collector can be operated, in a self-sufficient manner, for a longer period of time at an inaccessible location by means of a battery supply. There are various solutions in the prior art.

U.S. Pat. No. 6,840,121 B2 discloses for example a self-sufficient, self-powered multiple-sample collector for fluids, in particular liquids, in which ten piston pumps in the form of syringes are vertically arranged in a cylindrical support frame. Each piston is preloaded by means of a compression spring. Upon triggering, the spring is relaxed and in so doing pulls the piston back such that liquid is sucked in through a needle-shaped opening in the syringe.

Spiral springs (or helical springs) can be designed as compression springs (helical compression springs) or as extension springs (helical extension springs). Compression springs can be subjected to pressure and pushed together under pressure (absorption of potential energy). When this pressure is relieved, they relax and can do work (release of the stored potential energy). Extension springs can be subjected to tension and are pulled apart under tension (absorption of potential energy). When this tension is relieved, they are pulled together and can do work (release of the stored potential energy).

Piston pumps or syringes are also known in particular for use in aquatic environments from the multiple-sample collectors disclosed for example in U.S. Pat. No. 6,187,530 B1 and in the brochure entitled "Spritzenprobennehmer K/MT 115-Meerestechnisches Gerät zur Wasserprobennahme" from K.U.M Umwelt-und Meerestechnik Kiel GmbH. In this document, the pistons of the syringes are displaced by motorized means rather than in a spring-operated manner, however.

Various multiple-sample collectors comprising piston pumps are described in the following cited documents. In U.S. Pat. No. 4,116,067 A, the end of the piston that is remote from the piston pump is guided in a spiral-shaped slot such that rotating the piston pump in the slot plane results in the piston being displaced. In U.S. Pat. No. 4,288,206 A, the pistons are displaced by motorized means, in that they are fastened to a common bearing beam which is moved vertically upwards and downwards by means of an eccentric. In WO 96/30 740 A2, the piston is displaced by means of a vertical spindle. US 2010/0247378 A1 discloses a piston pump which is used both to receive fluid and to dispense fluid; the piston is displaced by motorized means in this case. U.S. Pat. Nos. 5,201,720 A, 5,800,405 A and WO 2012/085 580 A1 disclose piston pumps each having two spiral springs for displacing the piston. US 2006/0069 354 A1 discloses a piston pump in the form of a syringe, in which the piston is loaded by means of four compression springs, with each two compression springs working against one another such that they tension one another in a reciprocal manner.

U.S. Pat. No. 3,884,081 A describes an automated multiple-sample processor designed as a multiple-sample collector for air, comprising four piston pumps in the form of syringes which have a sample opening, a cylindrical housing and an axially displaceable piston and which are removably mounted in a support frame. Each piston is connected to an unguided spiral spring, which is designed as an extension spring and is supported in the support frame, by means of the free end of said piston that is remote from the needle opening as the sample opening. In the tensioned initial position, the extension spring is pulled apart and locked, and the piston is retracted into the cylindrical housing of the syringe. The lock has a release lever that can be actuated by a driver on a rotatable shaft. The rotatable shaft is connected to a motor drive. When the release lever is actuated by the driver, the fixed extension spring is unloaded, is pulled together and displaces the piston by pulling it out of the cylindrical housing of the syringe. At the same time, an air sample is sucked in through the needle opening located in the medium to be sampled. A particularity of this known multiple-sample collector is that the needle opening is closed at the same time as the air sample is drawn in order to securely confine the drawn air sample.

SUMMARY

In an embodiment, the present invention provides an automated multiple-sample processor for fluid samples. The automated multiple-sample processor includes a plurality of piston pumps which have a sample opening, a cylindrical housing and an axially displaceable piston and which are removably mounted in a support frame. Each of the pistons are connected to first and second spiral springs by a free end of the piston that is remote from the sample opening. The two spiral springs are supported in the support frame and are fixable in a tensioned initial position by a lock which, for each of the piston pumps, has a release lever triggerable by a driver on a rotatable shaft in a manner such that the triggering of the release lever results in the piston being displaced in the cylindrical housing. The two spiral springs are both configured either as extension springs or as compression springs. In the case the two spiral springs are provided as the extension springs with the release lever in a first installation position I, the triggering of the release lever by the driver results in the piston being pushed into the cylindrical housing. In the case the two spiral springs are provided as the compression springs with the release lever in a second installation position II, which is rotated by 180° with respect to the first installation position I, the triggering of the release lever by the driver results in the piston being pushed out of the cylindrical housing.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
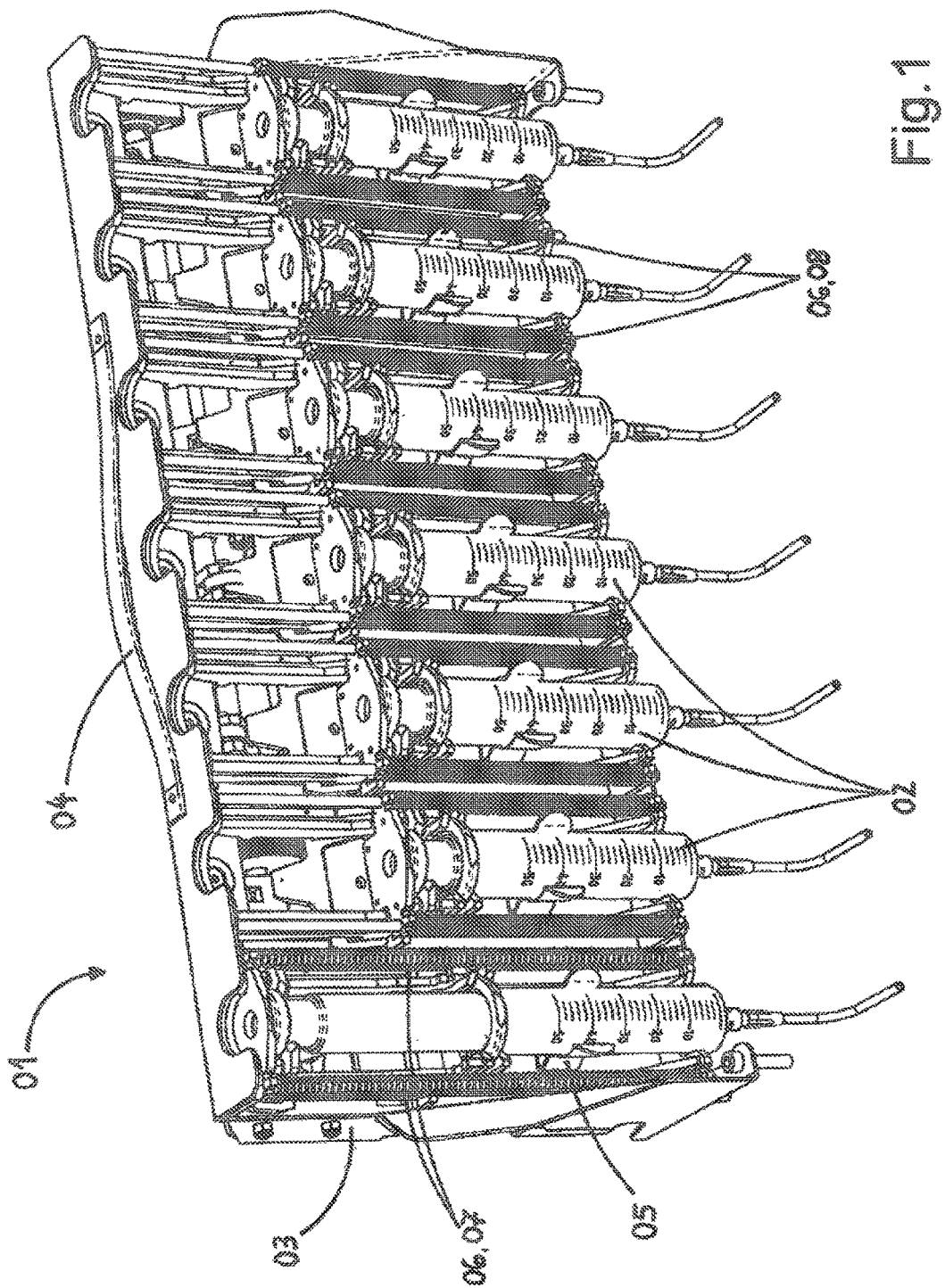
FIG. 1 is a perspective view of the front of the multiple-sample processor.

All the previous multiple-sample processors that have been described are designed exclusively for sampling, hence the common designation as "sample collectors". Since, however, in many applications there are often also reactions by organisms that are present in the examination field to influences of the surrounding medium, it is recognized according to an embodiment of the present invention that is also desirable for substances to be able to be dispensed into the environment. The optimum case according to an embodiment of the present invention would therefore be combined sample-taking and sample-dispensing. Proceeding from the last-mentioned document, U.S. Pat. No. 3,884,081 A, an embodiment of the present invention solves the problem of developing the multiple-sample processor of the type in question such that it can be used both to take samples from the environment and to dispense samples into the environment. In this case, its design is as simple and variable as possible, but also is impervious to environmental influences, and cost-effective nonetheless.

The multiple-sample processor is characterized according to an embodiment of the invention in that each piston is connected, by means of the free end thereof that is remote from the sample opening, to two spiral springs which are both designed either as extension springs or as compression springs, and in that either two extension springs and the release lever are provided for each piston in a first installation position I, the triggering of the release lever by the driver resulting in the piston being pushed into the cylindrical housing, or two compression springs and the release lever are provided for each piston in a second installation position II, which is rotated by 180° with respect to the first installation position I, the triggering of the release lever by the driver resulting in the piston being pushed out of the cylindrical housing.

The multiple-sample processor according to an embodiment of the invention is designed to be reversible, such that each piston pump can be individually set to either receive a sample or dispense a sample (reversal) upon triggering. In this context, the term "sample" should be understood to mean any kind of liquid or gaseous substance, thus not only those which are subjected to a subsequent analysis, but also those substances which are used to prepare/influence the analysis by changing the environment. The multiple-sample processor according to an embodiment of the invention makes it possible to carry out whole series of processes with two different process steps in a fully automatic manner. For example, a first piston pump can be filled with a toxic substance at a time $t_1$, and this substance can be dispensed into an enclosed volume upon triggering. Samples are then drawn by the second, third and fourth piston pumps at times $t_2$, $t_3$ and $t_4$ in order to be able examine the effect of the toxic substance on the organisms in the volume which is for example enclosed in a benthic chamber. A fifth piston pump is then triggered at a time $t_5$ which in turn dispenses a toxic substance into the volume. Samples are then in turn taken by the sixth and seventh piston pumps at times $t_6$ and $t_7$. Alternatively, it is also possible for a substance to be dispensed only at the time $t_1$ and for samples to be drawn at all other times in order to document the temporal impact of the substance.

All the piston pumps are accordingly preloaded in their springs before triggering. The extension springs are pulled apart, and the compression springs are pushed together. The alternating drawing and dispensing of samples by the correspondingly set-up piston pumps is only an example. Any other sequence is possible. It is also possible for some or even all of the piston pumps to be triggered at the same time. The triggering mode always depends on the type of application of the multiple-sample processor, however. Each piston pump is always triggered by a driver on the rotatable shaft. The triggering of each piston pump relative to the adjacent piston pump depends on the angular position of the driver on the shaft. The speed of each triggering process in turn depends on the rotational speed of the shaft.

In the multiple-sample processor according to an embodiment of the invention, it is particularly advantageous for the variable set-up of each piston pump for either sample-taking or sample-dispensing to be particularly simple in design. This variability is achieved by a simple release lever which can be arranged in two installation positions II. In this case, the lever is, however, mounted such that the drivers associated therewith on the rotatable shaft can trigger it in two installation positions I, II. In the first installation position I, the release lever interacts with two extension springs. In the tensioned initial position, the piston is therefore out of the cylindrical housing, which is filled with a substance; the piston pump is extended and the two extension springs are pulled apart and tensioned. When the release lever is triggered, they are pulled together and pull the piston forwards in the piston pump in the process. The substance introduced therein is dispensed through the sample opening. In the second installation position II, the release lever is installed so as to be offset by 180° (i.e. reversed) and interacts with two compression springs. In the tensioned initial position, the piston is in the cylindrical housing, which is empty; the piston pump is retracted and the two compression springs are pushed together. When the release lever is triggered, said springs are expanded and pull the piston backwards in the piston pump in the process. A sample is sucked into the cylindrical housing through the sample opening.

A particular advantage of the multiple-sample processor according to an embodiment of the invention is the ability of each piston pump to be freely set after triggering to operate as a sample collector or a sample dispenser. The multiple-sample processor according to the invention therefore allows a modular design. This modular design can be preferably and advantageously improved according to a first advantageous embodiment of the invention by each piston pump being removably mounted in a separate module frame, the module frame being removably arranged in the support frame, and by the two spiral springs and the release lever being supported in the first or second installation position I, II in the module frame. Each piston pump therefore has its own storage rack and can already be preloaded therein since the springs are then also supported in the module frame. All the module frames together with the preloaded piston pumps can then be installed in the support frame. Simply removing each module frame allows the release lever to be simply converted from one installation position I, II into the other installation position I, II. No tools are required for this process. It is also possible, however, to have two types of alternatively set-up module frames available, and to combine these in the support frame according to the requirements (number of piston pumps for receiving a sample, number of piston pumps for dispensing a sample).

Piston pumps are available on the market in various embodiments. The simplest form of a manually operable piston pump constitutes the syringe known from medicine. Larger syringes appear in various embodiments and are used accordingly for research purposes. It is therefore particularly advantageous and preferable according to a next embodiment of the invention for the piston pump of a syringe to be formed with a needle opening as the sample opening and for the cylindrical housing to have a radially circumferential first flange and for the free end of the piston to have a radially circumferential second flange, the first flange being introduced into a stationary receiving portion and the second flange being introduced into a displaceable receiving portion in the support frame or in the module frame, and the two spiral springs being connected at one end thereof to the support frame or the module frame, and at the other end thereof to the displaceable receiving portion. Syringes for which both the housing and the piston have a radially circumferential flange are preferably used in the multiple-sample processor according to an embodiment of the present invention. The cylindrical housing of the syringe is mounted in the support frame or in the module frame in a defined manner by means of the first flange. The piston is connected to the two springs by means of the second flange, and can thus be securely displaced thereby in the cylindrical housing when said springs are relaxed. It is further particularly advantageous and preferable, when the piston pump is designed as a syringe, for the syringe to be made of glass and to have a piston displacement of 50 ml, the piston being displaceable in the cylindrical housing in an airtight manner. Glass syringes are particularly stable, but are also highly transparent, which allows the inside of the syringe to be easily observed (for example for in situ observation of a sample that is still inside the housing, thus without transferring the sample into an external vessel). A piston displacement of 50 ml allows a sample to be obtained or dispensed to a degree that is easy to manage for research purposes. Enclosing the piston in the cylindrical housing in an airtight manner ensures that no sample material is lost or is contaminated by secondary drawing. In this case, the use of glass for the airtight hold is particularly suitable because it can be produced by grinding in a relatively simple, but durable, manner. Plastics syringes are prone to changing shape due to aging and overloading, and are thus prone to leakage.

A further advantage of the multiple-sample processor according to an embodiment of the invention consists in the ability of each piston pump to be easily converted between a suction operation and an ejection operation. In this case, it is particularly advantageous and preferable according to a next embodiment of the invention for the release lever to be formed in three parts, namely two spacer levers and a cam lever, the cam lever being hingedly arranged on one end of the spacer levers, and the spacer levers being connected to the support frame or the module frame in a first installation position I or in a second installation position II, which is rotated by 180° with respect to the first installation position I. Parts of this kind can be produced particularly easily, for example by cutting using a water jet. Both parts are hingedly, i.e. rotatably, hooked into one another. High operational reliability is ensured by avoiding complicated hinged joints. This is of great importance in particular for the self-sufficient use of the multiple-sample processor in inaccessible areas, for example in waters of great depth, in which it has to operate self-sufficiently for a longer period of time. The same applies to the preferred and advantageous use of a rotatable shaft, which is designed as a camshaft that is capable of bidirectional rotation and comprises axially adjustable cams as drivers. A camshaft of this kind, which can be operated in both circumferential directions and on which the cams can be positioned at any desired points, are commercially available, cost-effective and very robust. The same applies in turn to the next preferred embodiment of the invention, in which the rotatable shaft can be driven by a pressure-neutral DC motor having an incremental encoder. A pressure-neutral DC motor is filled with oil, the oil filling being sealed by a pressure-proof rotary seal. Said motor can be reliably used in both directions of rotation even in waters of great depth. An incremental encoder operates the DC motor as a stepper motor, as a result of which triggering times can be established which can be set in a temporally very accurate manner and so as to be precisely mutually spaced. It is of great importance in particular in scientific experiments to identify the precise times at which samples are taken following a contamination.

In terms of the materials that can be used, it is preferable and advantageous in the multiple-sample processor according to an embodiment of the present invention for the module frame and/or the stationary and the displaceable receiving portion to be made of fiber-reinforced plastics material and/or for the support frame to be made of metal and/or for the spiral springs to be made of stainless steel. The fiber-reinforced plastics material can be easily processed for example by water-jet cutting. A simple metal for the support frame can be easily bent. Stainless steel for the spiral springs prevents them being damaged during operation. If an operation in water, optionally even in salt water, is intended, all the components used naturally have to be water- and corrosion-resistant. Spiral springs made of stainless steel are already inherently very stable and can thus be loaded with ease. In order to further improve stability, and in particular to avoid bending, according to a next embodiment of the invention, yet more preferably and advantageously, each spiral spring (extension and compression) can have a central guide rod which is mounted in the support frame or in the module frame. Said guide rod can be made of metal or stainless steel, or even of plastics material.

A plurality of piston pumps is always provided in the multiple-sample processor according to an embodiment of the present invention. Depending on the application, this may be at least two piston pumps (both for suction or ejection operation, or one for suction operation and one for ejection operation) or may be up to ten or even more piston pumps (all for suction or ejection operation, or some for suction operation and some for ejection operation). As already stated above in an embodiment for one application, experience has shown it to be particularly advantageous and preferable for seven piston pumps to be mounted in parallel beside one another in the support frame. Finally, for the handleability of the multiple-sample processor according to an embodiment of the invention, it is also particularly practical for a carrying handle to be arranged on the upper side of the support frame. This allows the multiple-sample processor to be transported particularly easily, and optionally heaved and sent down a rope into inaccessible areas. Further design-related embodiment details regarding the multiple-sample processor and its preferred embodiments can be found in the following description of embodiments.

FIG. 1 shows an automated multiple-sample processor 01 in the perspective front view. The multiple-sample processor 01 shown is used to take water samples ("water sample collector", WSC) in the deep sea. In the embodiment shown, it comprises seven piston pumps 02 which are arranged in parallel beside one another in a support frame 03. A carrying handle 04, for example a belt strap, is arranged on the upper side of the support frame 03 for easy handling. The piston pumps 02 are removably mounted in clamps 05 and are in a preloaded state. In the embodiment shown, it can be seen that the left-hand piston pump 02 is filled with a substance, which is dispensed into the environment upon triggering. The other piston pumps 02 are empty and are withdrawn upon triggering in order to take water samples from the environment.

It can also be seen in FIG. 1 that each piston pump 02 is surrounded by two spiral springs 06. For the left-hand piston pump 02 these are two extension springs 07, and for the remaining piston pumps 02 these are two compression springs 08 in each case. In addition, the cam plate 33 can be seen for each piston pump 02 (compare with FIG. 3), which plate is used to trigger the spiral springs 06 by means of the cams 12 of the camshaft 10 (compare with FIG. 2).

Figure 2:
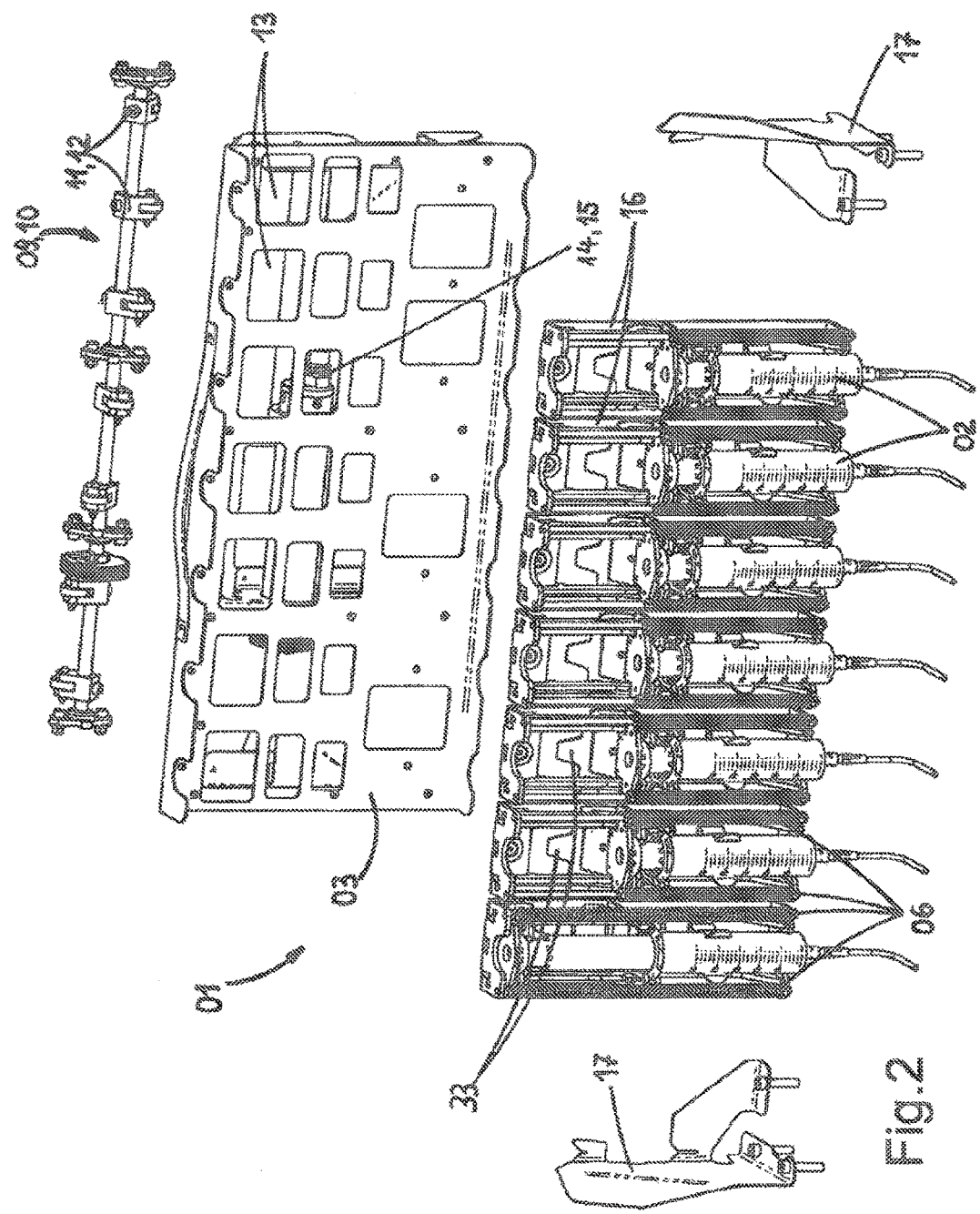
FIG. 2 is an exploded perspective view of the multiple-sample processor.

FIG. 2 is an exploded view of the automated multiple-sample processor 01 according to FIG. 1. This figure shows the support frame 03 and a rotatable shaft 09 arranged therebehind in the form of a camshaft 10 that has a plurality of drivers 11 designed as cams 12. The cams 12 engage in the support frame 03 through recesses 13. A drive 14 for the rotatable shaft 09 can also be seen through these recesses, which drive is a pressure-neutral DC motor 15 having an incremental encoder in the chosen embodiment. This figure also shows seven separate module frames 16 in which the piston pumps 02 and the spiral springs 06 are arranged. All the module frames 16 are held on the support frame 03 and stabilized by side parts 17.

Figure 3:
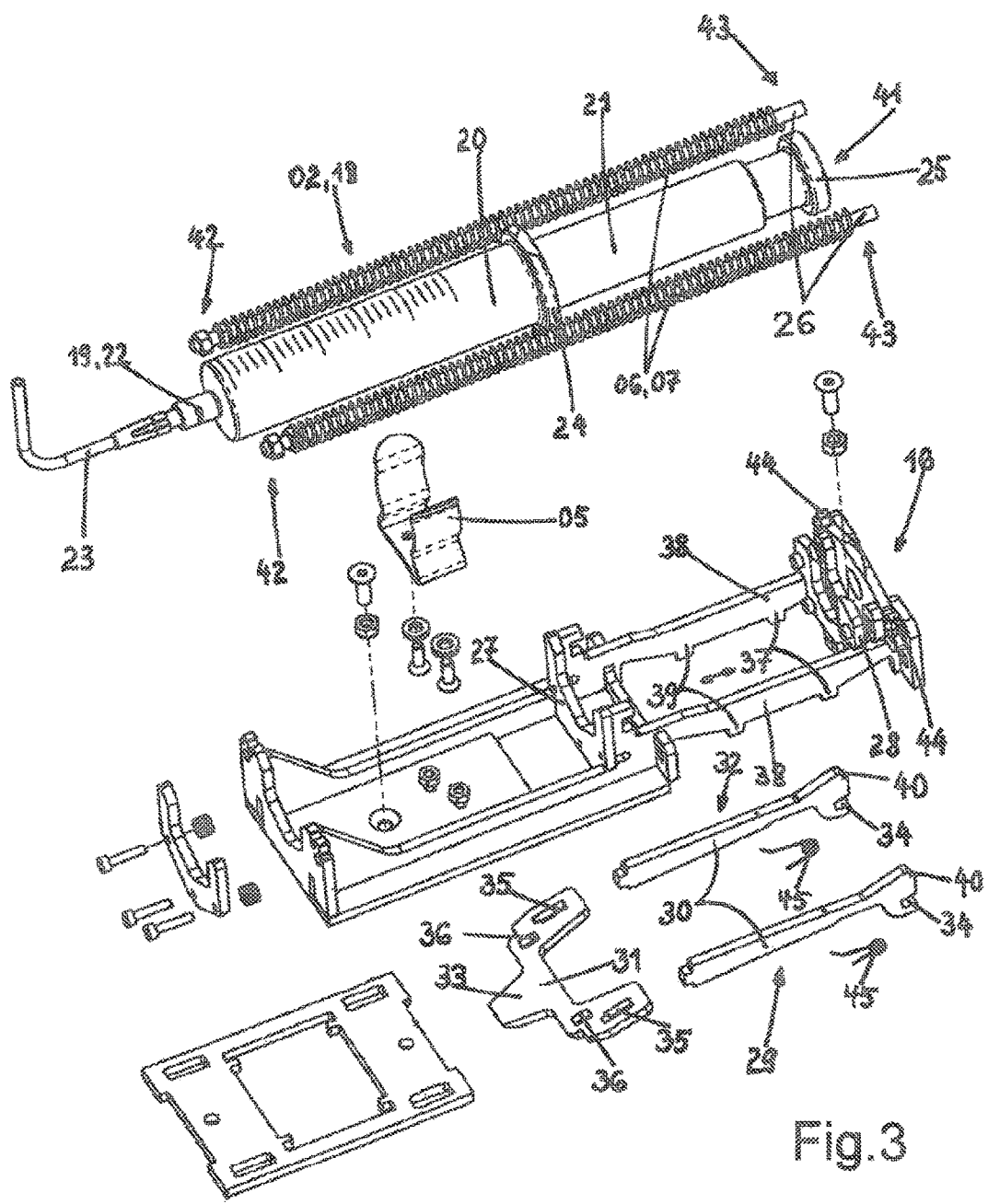
FIG. 3 is an exploded perspective view of the multiple-sample processor in the region of a piston pump.

FIG. 3 is an exploded view of a module frame 16 comprising a piston pump 02. The piston pump 02 is designed as a glass syringe 18 in the embodiment shown. It consists of a sample opening 19, a cylindrical housing 20 and an axially displaceable piston 21. A bent attachment 23 for directed ejection or suction of sample water is located on the sample opening 19 in the form of a needle opening 22. Furthermore, a radially circumferential first flange 24 can be seen on the cylindrical housing 20, and a radially circumferential second flange 25 can be seen on the piston 21.

In this case, the second flange 25 is arranged on the free end 41 of the piston 21 that is remote from the sample opening 19, at which end the spiral springs 06 are also connected to the piston 21 by means of the displaceable receiving portion 28 (compare with description of the module frame 16; see below). Two guide rods 26 are arranged on either side of the syringe 18, which rods are mounted in the support frame 03 or in the module frame 16 and on which the spiral springs 06 are guided. The left-hand piston pump 02 according to FIG. 1 is shown, and therefore the two spiral springs 06 are the extension springs 07. The piston 21 is shown to be maximally withdrawn out of the cylindrical housing 20. The extension springs 07 (analogously to compression springs 08) are rigidly connected at one end 42 thereof to the support frame 03 or the module frame 16 or to the stationary receiving portion 27 and at the other end 43 thereof to the displaceable receiving portion 28.

The module frame 16 is shown below the piston pump 02 and is screwed into the support frame 03. The clamp 05 in which the syringe 18 is removably clamped can be seen. Furthermore, a stationary receiving portion 27 is shown in the module frame 16, into which portion the first flange 24 on the cylindrical housing of the syringe 18 is introduced. The cylindrical housing 20 of the syringe 18 is securely fixed in the module frame 16 thereby. There is also a displaceable receiving portion 28 in the module frame 16, into which portion the second flange 25 on the piston 21 is introduced. The two extension springs 07 are connected to this displaceable flange 25. When the extension springs 07 are triggered, they are pulled together and in so doing pull the displaceable receiving portion 28 and thus the piston 21 towards the sample opening 19. The contents of the syringe 18 are ejected by the attachment 23. The extension springs 07 or compression springs 08 are supported in the module frame 16. Since said frame is rigidly installed in the support frame 03, the spiral springs 06 are therefore also supported in the support frame 03. The extension springs 07 or compression springs 08 are rigidly connected at the other ends 43 thereof to lugs 44 on the displaceable receiving portion 28.

A lock comprising a release lever 29 for triggering the spiral springs 06 is shown below the module frame 16. Said lever is made of three parts and consists of two spacer levers 30 and a cam lever 31. The cam lever 31 is hingedly arranged on one end 32 of the spacer lever 30. In this case, the hinged joint consists of pins 34 on the spacer levers 30 and slots 35 in the cam lever 31. The cam lever 31 also has two recesses 36. Said recesses are positioned on first shoulders 37 on two frame struts 38 of the module frame 16 if the first installation position I (extension springs, compare with FIG. 4) and on second shoulders 39 on the frame struts 38 in the second installation position II (compression springs, compare with FIG. 5) which is rotated by 180°. Said hinged connections form the bearing point for the rotational movement of the cam lever 31 during triggering. The cam lever 31 has a cam plate 33 against which the cam 12 of the camshaft 10 acts. The release lever 29 is located in the module frame 16 below the displaceable receiving portion 28 of the syringe 18 and is loaded by tension springs 45 in the locked position. Upon triggering, the cam lever 31 is temporarily subjected to high pressure by the spring force and releases the two spacer levers 30 which retain the displaceable receiving portion 28 by means of projections 40 at the ends 32 of said levers. Said portion and the spiral springs 06 connected thereto are released upon triggering.

Figure 4:
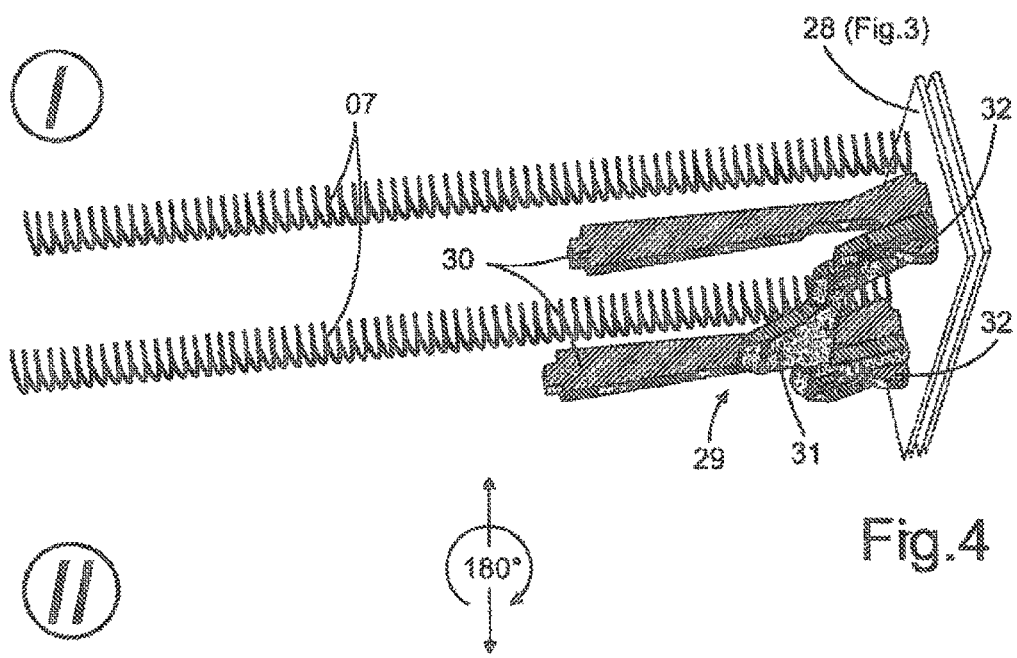
FIG. 4 shows a detail of the first installation position I of the release lever.
Figure 5:
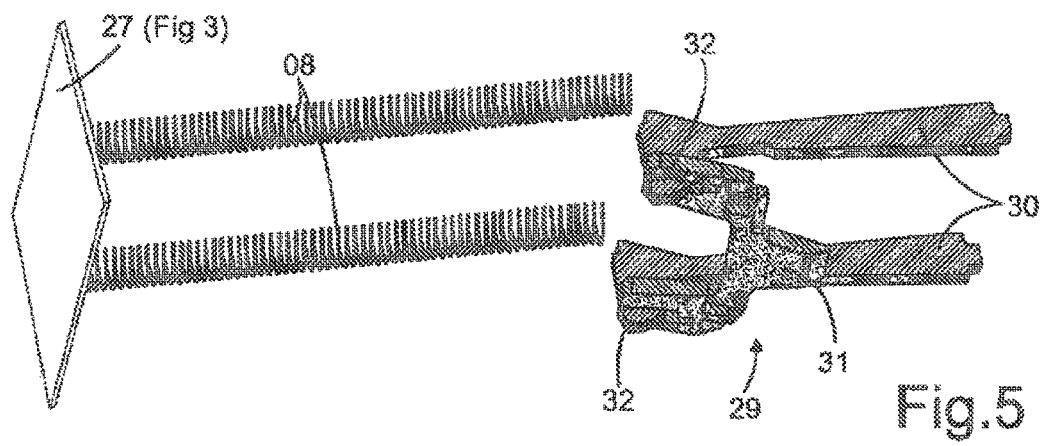
FIG. 5 shows a detail of the second installation position II, rotated by 180°, of the release lever.

FIGS. 4 and 5 show the release lever 29 in the two possible installation positions I, II thereof. In FIG. 4, the release lever 29 interacts with the two extension springs 07. The spacer levers 30 are oriented so as to have the ends 32 towards the displaceable receiving portion 28 (compare with FIG. 3) in the first installation position I. In FIG. 5, the release lever 29 is shown in the second possible installation position II thereof, which is simply rotated by 180° with respect to the first installation position I. In the second installation position II, the spacer levers 30 are oriented so as to have the ends 32 thereof towards the stationary receiving portion 27 (compare with FIG. 3). The release lever 29 interacts in this second installation position II with the two compression springs 08. Since all the parts remain inserted into one another, the conversion between the two installation positions I, II can take place particularly simply, without a tool.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE SIGNS 01 automated multiple-sample processor
02 piston pump
03 support frame
04 carrying handle
05 clamp
06 spiral spring
07 extension spring
08 compression spring
09 rotatable shaft
10 camshaft
11 driver
12 cam
13 recess in 03
14 drive
15 DC motor
16 module frame
17 side part of 03
18 syringe
19 sample opening
20 cylindrical housing
21 piston
22 needle opening
23 attachment
24 first flange on 20
25 second flange on 21
26 guide rod
27 stationary receiving portion for 24
28 displaceable receiving portion for 21
29 release lever
30 spacer lever
31 cam lever
32 one end of 30
33 cam plate
34 pin on 30
35 slot in 31
36 recess in 31
37 first shoulder on 38
38 frame strut
39 second shoulder on 38
40 projection on 30
41 free end of 21, remote from 19
42 one end of 06, 07, 08
43 other end of 06, 07, 08
44 lug on 28
45 tension spring
I first installation position of 29 (extension springs 07, ejection)
II second installation position of 29 (compression springs 08, suction)

The invention claimed is:

1. An automated multiple-sample processor for fluid samples, the automated multi-sample processor comprising:
a plurality of piston pumps which have a sample opening, a cylindrical housing and an axially displaceable piston and which are removably mounted in a support frame, each of the pistons being connected to first and second spiral springs by a free end of the piston that is remote from the sample opening, the two spiral springs being supported in the support frame and being fixable in a tensioned initial position by a lock which, for each of the piston pumps, has a release lever triggerable by a driver on a rotatable shaft in a manner such that the triggering of the release lever results in the piston being displaced in the cylindrical housing, the two spiral springs being both configured either as extension springs or as compression springs,
wherein, in the case the two spiral springs are provided as the extension springs with the release lever in a first installation position I, the triggering of the release lever by the driver results in the piston being pushed into the cylindrical housing, or, in the case the two spiral springs are provided as the compression springs with the release lever in a second installation position II, which is rotated by 180° with respect to the first installation position I, the triggering of the release lever by the driver results in the piston being pushed out of the cylindrical housing.

2. The automated multiple-sample processor according to claim 1, wherein each of the piston pumps is removably mounted in a separate module frame, the module frame being removably arranged in the support frame, and wherein the two spiral springs and the release lever are supported in the first installation position I or the second installation position II in the module frame.

3. The automated multiple-sample processor according to claim 1, wherein the piston pump of a syringe is formed with a needle opening as the sample opening, and the cylindrical housing has a radially circumferential first flange and the free end of the piston has a radially circumferential second flange, the first flange being introduced into a stationary receiving portion and the second flange being introduced into a displaceable receiving portion in the support frame or in the module frame, and the two spiral springs being connected at one end thereof to the support frame or the module frame, and at the other end thereof to the displaceable receiving portion.

4. The automated multiple-sample processor according to claim 3, wherein the syringe is made of glass and has a piston displacement of 50 ml, the piston being displaceable in the cylindrical housing in an airtight manner.

5. The automated multiple-sample processor according to claim 1, wherein each of the release levers is formed in three parts including two spacer levers and a cam lever, the cam lever being hingedly arranged on one end of the spacer levers, and the spacer levers being connected to the support frame or the module frame in the first installation position I or in the second installation position II, which is rotated by 180° with respect to the first installation position I.

6. The automated multiple-sample processor according to claim 1, wherein the rotatable shaft is configured as a camshaft that is capable of bidirectional rotation and comprises axially adjustable cams as the drivers.

7. The automated multiple-sample processor according to claim 1, wherein the rotatable shaft is driveable by a pressure-neutral DC motor having an incremental encoder.

8. The automated multiple-sample processor according to claim 2, wherein the module frame and/or the stationary and the displaceable receiving portion are made of fiber-reinforced plastics material and/or the support frame is made of metal and/or the spiral springs are made of stainless steel.

9. The automated multiple-sample processor according to claim 1, wherein each of the two spiral springs has a central guide rod which is mounted in the support frame or in the module frame.

10. The automated multiple-sample processor according to claim 1, wherein the plurality of piston pumps comprise seven piston pumps mounted in parallel beside one another in the support frame.

11. The automated multiple-sample processor according to claim 1, wherein a carrying handle is arranged on the upper side of the support frame.

* * * * *